US010500082B1

(12) United States Patent
Elsmo

(10) Patent No.: US 10,500,082 B1
(45) Date of Patent: Dec. 10, 2019

(54) QUICK DEPLOYMENT CAST

(71) Applicant: IRON HORSE PRIME, LLC, Northbrook, IL (US)

(72) Inventor: Alan Clark Elsmo, Northbrook, IL (US)

(73) Assignee: IRON HORSE PRIME, LLC, Northbrook, IL (US)

( * ) Notice: Subject to any disclaimer, the term of this patent is extended or adjusted under 35 U.S.C. 154(b) by 1105 days.

(21) Appl. No.: 14/805,460

(22) Filed: Jul. 21, 2015

Related U.S. Application Data

(60) Provisional application No. 62/119,806, filed on Feb. 23, 2015.

(51) Int. Cl.
  *A61F 5/00* (2006.01)
  *A61F 5/058* (2006.01)
(52) U.S. Cl.
  CPC ................ *A61F 5/05816* (2013.01)
(58) Field of Classification Search
  CPC .... A61F 5/058; A61F 5/0585; A61F 5/05858; A61F 5/05866; A61F 5/05841; A61F 5/05833; A61F 5/05816
  USPC .................................................... 602/6–8, 13
  See application file for complete search history.

(56) References Cited

U.S. PATENT DOCUMENTS

| | | |
|---|---|---|
| 3,785,375 A | 1/1974 | Lipson |
| 3,930,496 A | 1/1976 | Gibbons |
| 4,019,506 A | 4/1977 | Eschmann |
| 4,309,990 A | 1/1982 | Brooks |
| 4,483,332 A | 11/1984 | Rind |
| 4,498,467 A | 2/1985 | Kirkpatrick |
| 4,502,479 A | 3/1985 | Garwood et al. |
| 4,996,979 A | 3/1991 | Grim et al. |
| 5,288,286 A | 2/1994 | Davis et al. |
| 5,318,504 A | 6/1994 | Edenbaum et al. |
| 6,695,801 B1 | 2/2004 | Toronto et al. |
| 2006/0004313 A1* | 1/2006 | Heinz ........................ A61F 5/01 602/7 |
| 2009/0171356 A1 | 7/2009 | Klett |
| 2009/0204047 A1* | 8/2009 | MacArthur ............... A61F 5/01 602/36 |
| 2013/0324897 A1 | 12/2013 | Martin |
| 2014/0107550 A1 | 4/2014 | Paulson |

FOREIGN PATENT DOCUMENTS

| | | |
|---|---|---|
| BE | 1017372 A3 | 7/2008 |
| JP | S51115093 A | 10/1976 |
| JP | S58175561 A | 10/1983 |

(Continued)

OTHER PUBLICATIONS

PCT International Search Report for PCT/US2016/043304 (related application), dated Nov. 2, 2016.

(Continued)

*Primary Examiner* — Kim M Lewis
(74) *Attorney, Agent, or Firm* — Flener IP & Business Law; Zareefa B. Flener

(57) ABSTRACT

A quick deployment cast comprises a flexible outer sleeve fitted for a human appendage. The cast has a bladder network within the sleeve, a fluid capable of expanding and hardening when in the presence of a curing agent, stored within the bladder network and a mechanism for exposing the fluid to the curing agent.

12 Claims, 14 Drawing Sheets

(56) References Cited

FOREIGN PATENT DOCUMENTS

| JP | H05503860 A | 6/1993 |
|----|----|----|
| WO | 9105526 A1 | 5/1991 |
| WO | 02067832 A1 | 9/2002 |
| WO | WO2014088459 | 6/2014 |

OTHER PUBLICATIONS

PCT Written Opinion for PCT/US2016/043304 (related application), dated Nov. 2, 2016.
PCT Written Opinion of the International Searching Authority for PCT/US2016/043304 (related application); dated Nov. 2, 2016.
Notification of Reason(s) for Refusal, Patent Application No. 2018-523368, Dispatch Date: May 9, 2019, Representative/Applicant: AI Association of Patent and Trademark Attorneys (JP Office Action).
Supplementary European Search Report, Applciation No. EP 16 83 1095, Place of Search: Munich: Date of Completion of the Search: Mar. 19, 2019.
EP Office Action, CF Form 1507, EP Application No. 16 831 095.1.

* cited by examiner

QUICK DEPLOYMENT CAST

CROSS-REFERENCES TO RELATED APPLICATIONS

This application claims priority from U.S. Provisional Application Ser. No. 62/119,806 filed Feb. 23, 2015, which is hereby incorporated herein by reference in the respective in its entirety.

TECHNICAL FIELD

This invention relates to casts in medical applications in orthopedics, including specific applications for military field use and prevention of compartment syndrome. Utilizing a method and device along with an algorithm comparing normative and patient-specific data, the user and practitioner are provided with early detection for complications associated with immobilizing a traumatized limb.

BACKGROUND OF THE INVENTION

The subject invention generally relates to casting, monitoring, alerting and removing casting materials. Typically, application and removal of casts on a broken or sprained limb requires special tools, materials and expertise. These present challenges including superficial and cosmetic inconveniences, in addition to life-threatening and longer-term risks, such as lung cancers from chronic inhalation of fiberglass shavings. Additionally, trauma and compression of a limb through casting can lead to compartment syndrome which can require procedures that present significant risk and downside for the patient and orthopedic community.

BRIEF SUMMARY OF EMBODIMENTS OF THE INVENTION

According to one embodiment of the invention,

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
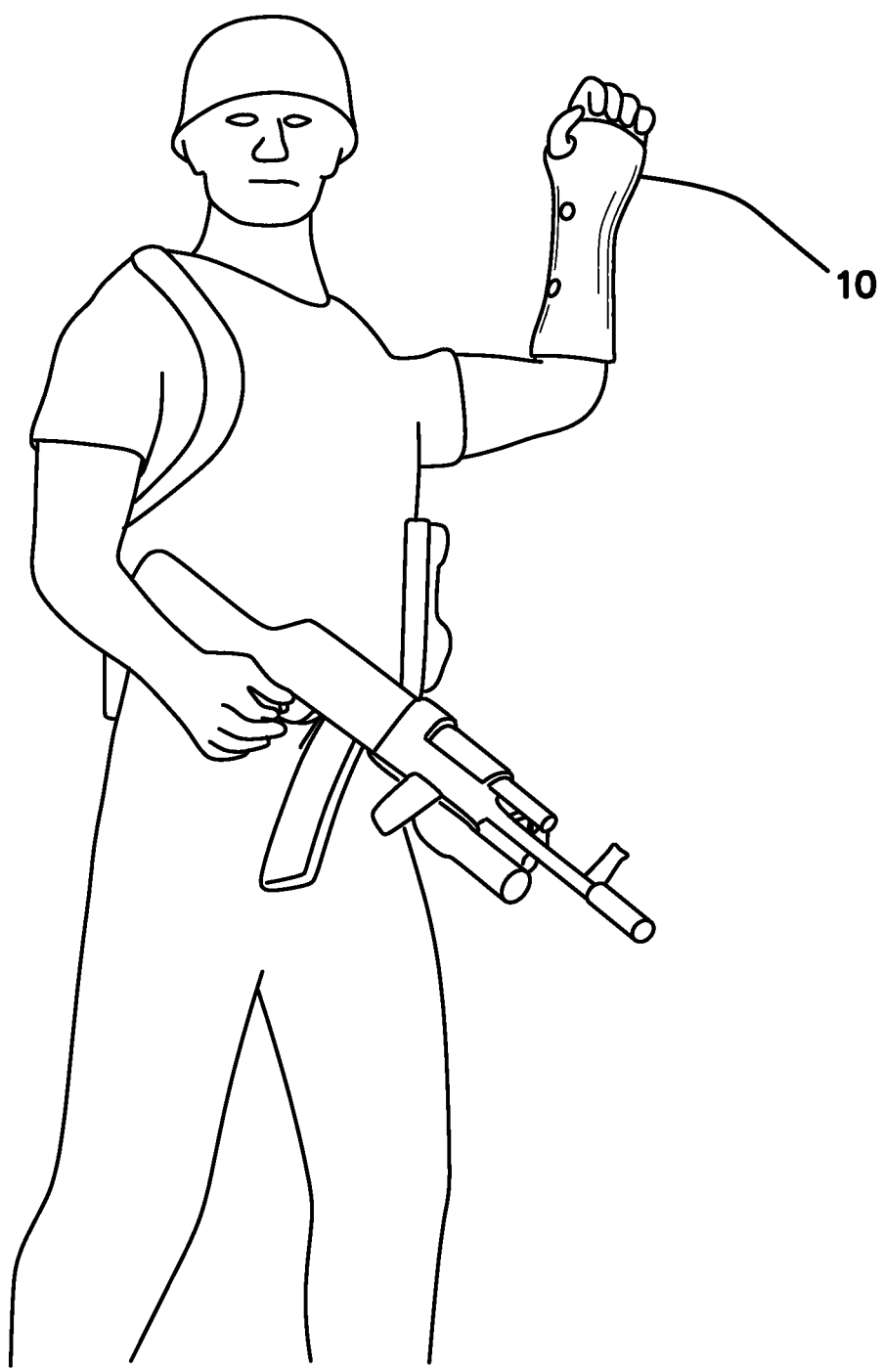
FIG. 1 is a perspective view of the quick deployment cast in use in a military application.
Figure 2:
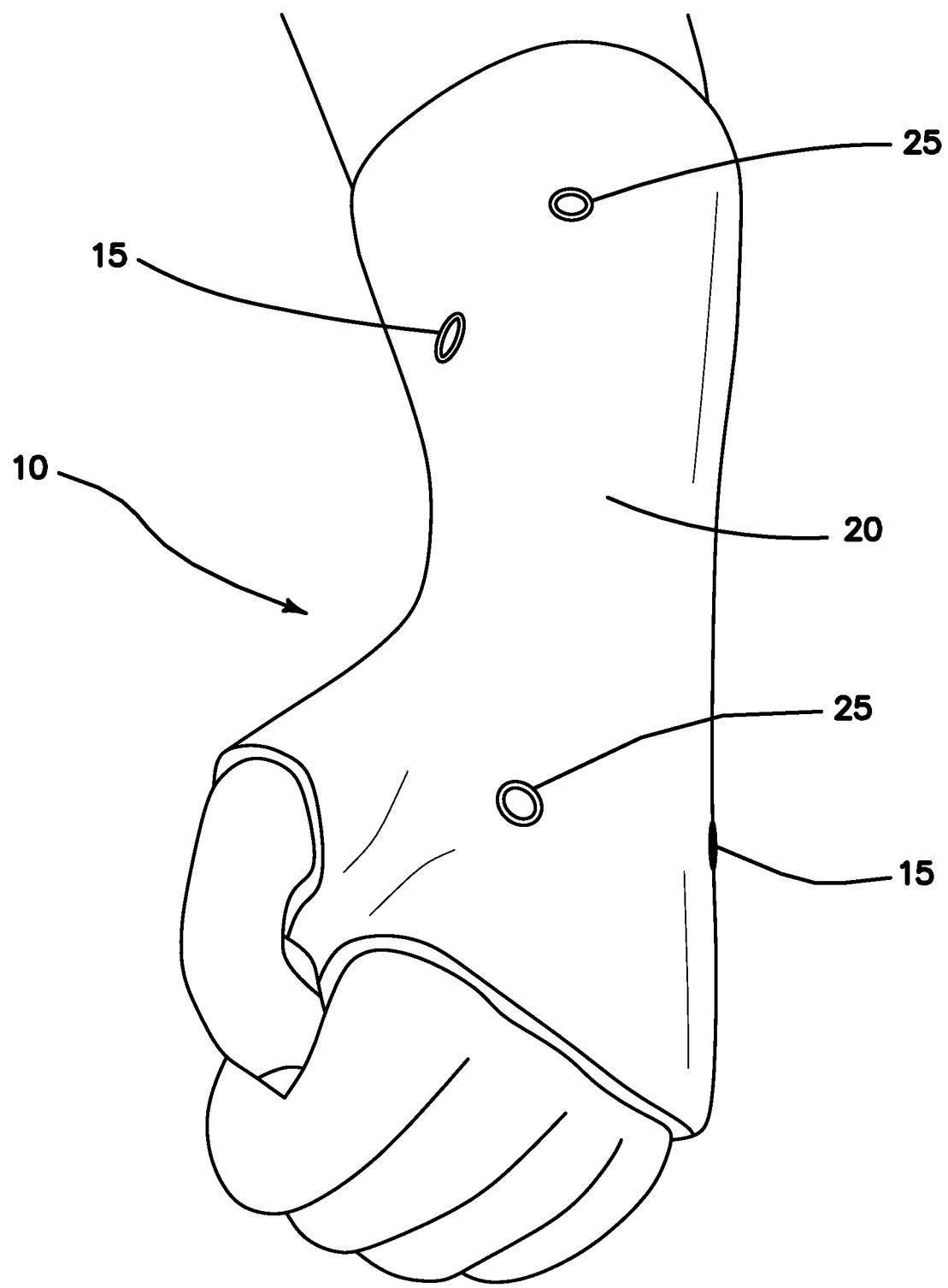
FIG. 2 is a perspective view of the quick deployment cast.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The following terms are used throughout this document:
cast 10
check valve ports 15
release mechanism 18
sleeve 20
balloon ports 25
bladder tubes 30
polyurethane gel 35
sensors 40 balloons 45
graphene wires 55
lines 60
seams 65
brace 70
bilateral sleeves 75

The present invention is directed toward a cast 10 or splint or tourniquet for a broken or traumatized limb that may be quickly and easily deployed in the battlefield or any other environment that is remote from a hospital. The invention may also be used in a hospital or clinic environment. The quick deployment cast 10 may be used as a tourniquet, with desired pressure being selected, thereby allowing the device to expand to create greater tension/pressure against the limb.

In a variant, referring to FIGS. 1-5 and 10-12, the cast comprises a sleeve 20 having a graphene fabric outer covering. The cast is pulled onto the wearer's limb similar to pulling on a sock. The cast includes a number of check valve ports 15 and a number of balloon ports 25. The valves 15 have a release mechanism 18 that when actuated permit air to enter the valve and enter bladder tubes 30. The cast 10 has a framework consisting of a web or network of bladder tubes 30 (which preferably are made of a graphene material) that is covered by the fabric outer covering, which is graphene or other fabric. The bladder network 30 may be oriented in any combination of patterns, including but not limited to double, triple or quadruple helical, with one set of tubes running parallel and another helical set intersecting the first set a various points.

Figure 3:
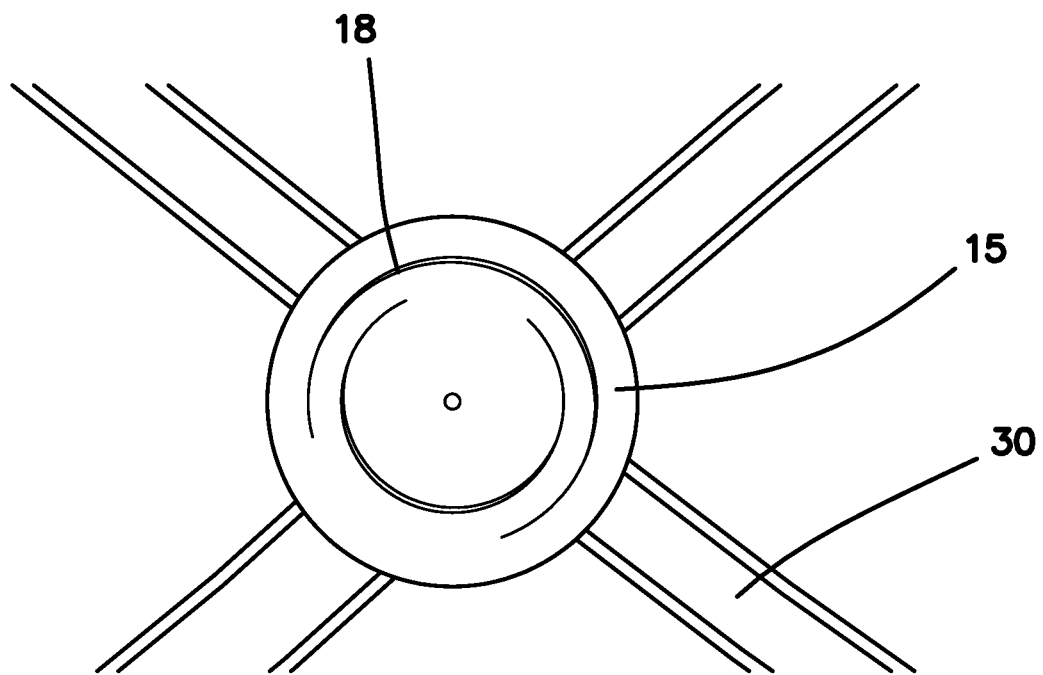
FIG. 3 is a detail view of a check valve port of the quick deployment cast.
Figure 13:
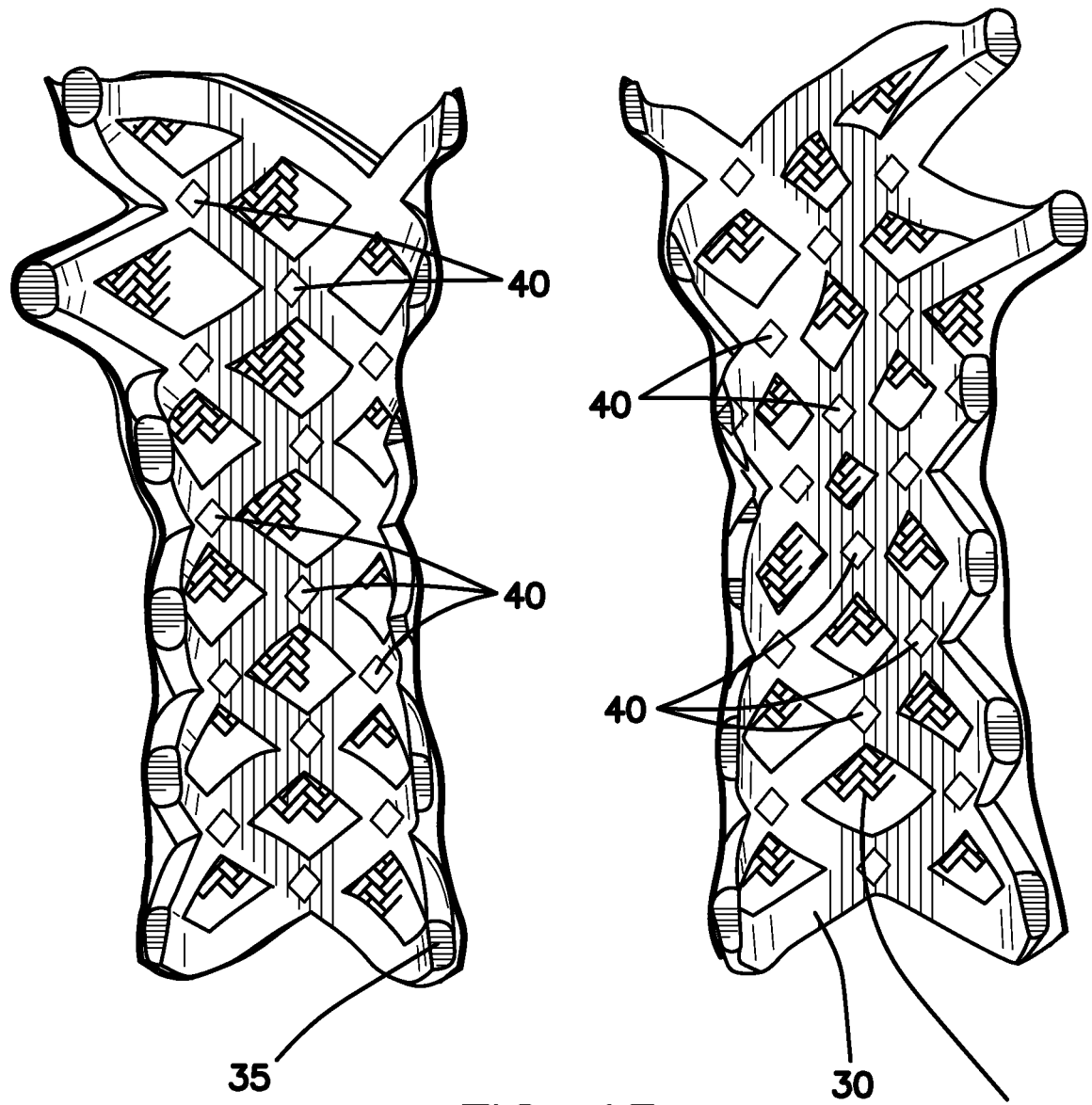
FIG. 13 is a cut away view of the bladder network of the quick deployment cast with the surrounding sleeve.
Figure 14:
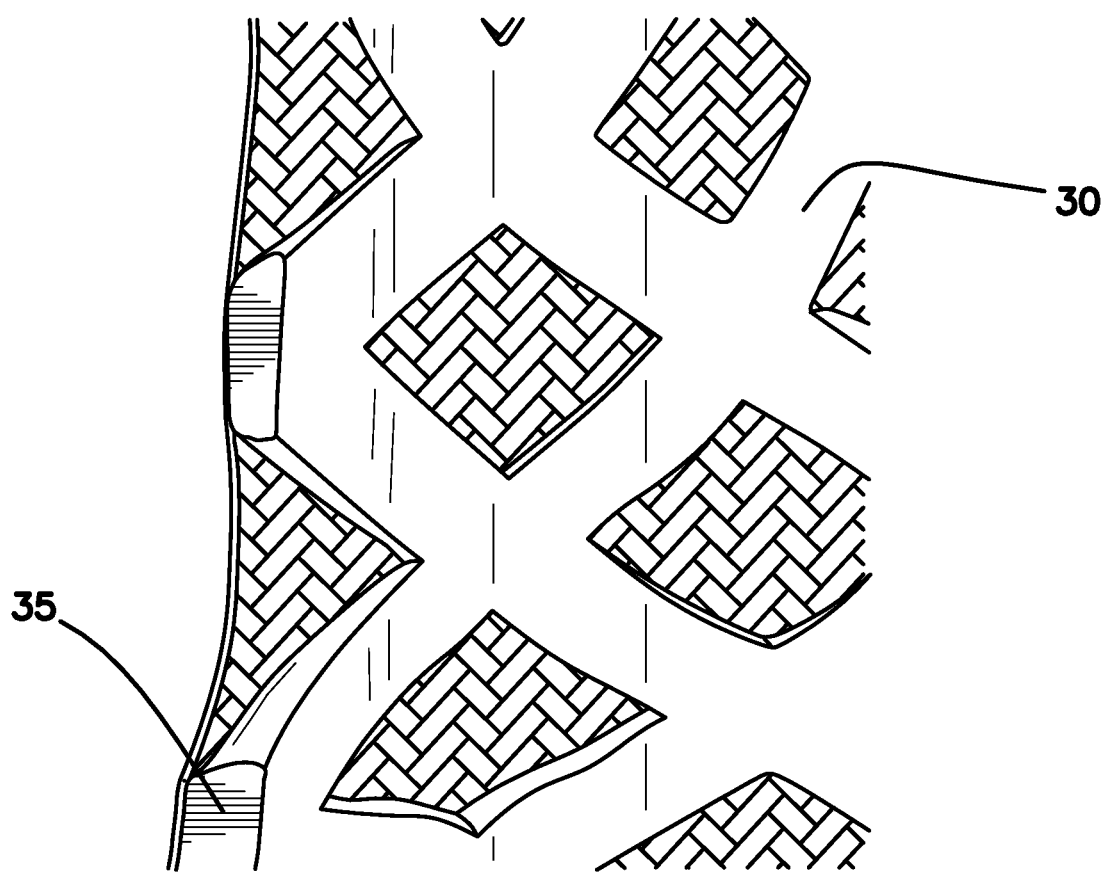
FIG. 14 is a detail view of the bladder network of the quick deployment cast.

Referring also to FIGS. 13-14, the bladder tubes 30, which are in fluid communication with the check valve 15 and balloon ports 25, contain a polyurethane gel 35. The polyurethane gel expands to a multiple of its initial volume (depending on desired properties like rigidity) when exposed to air. Referring to FIG. 3, when the cast is stored in a state ready for use, the interiors of the tubes 30 containing the gel are kept at near vacuum, with the check valves 15 closed, and the overall device compressed like a spring.

In an optional variant, a cellulose sponge is embedded in the bladder network 30, and the sponge is soaked in the polyurethane gel. In a variant, the sponge is a dehydrated, compressed cellulose sponge. The soaked sponge and polyurethane gel are activated by water that is introduced from reservoirs atop the check-valves when the sleeve is pulled onto the limb, similar to the variant having polyurethane and graphene spires within the bladder. The bladder tubes 30, which are in fluid communication with the check valve 15 and balloon ports 25, contain the sponge soaked polyurethane gel 35, and the sponge-gel may expand to a multiple of 3 to 4 times (or more) its initial volume when exposed to water.

Figure 4:
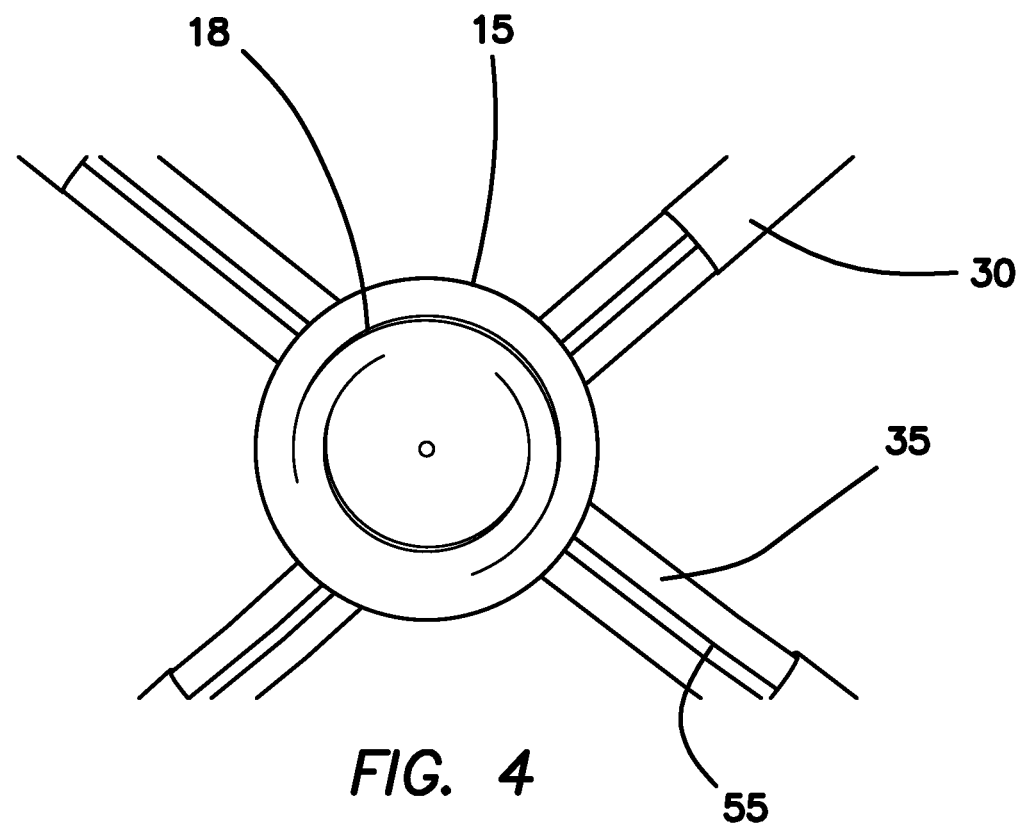
FIG. 4 is a detail view of a check valve port of the quick deployment cast with polyurethane gel deployed.
Figure 5:
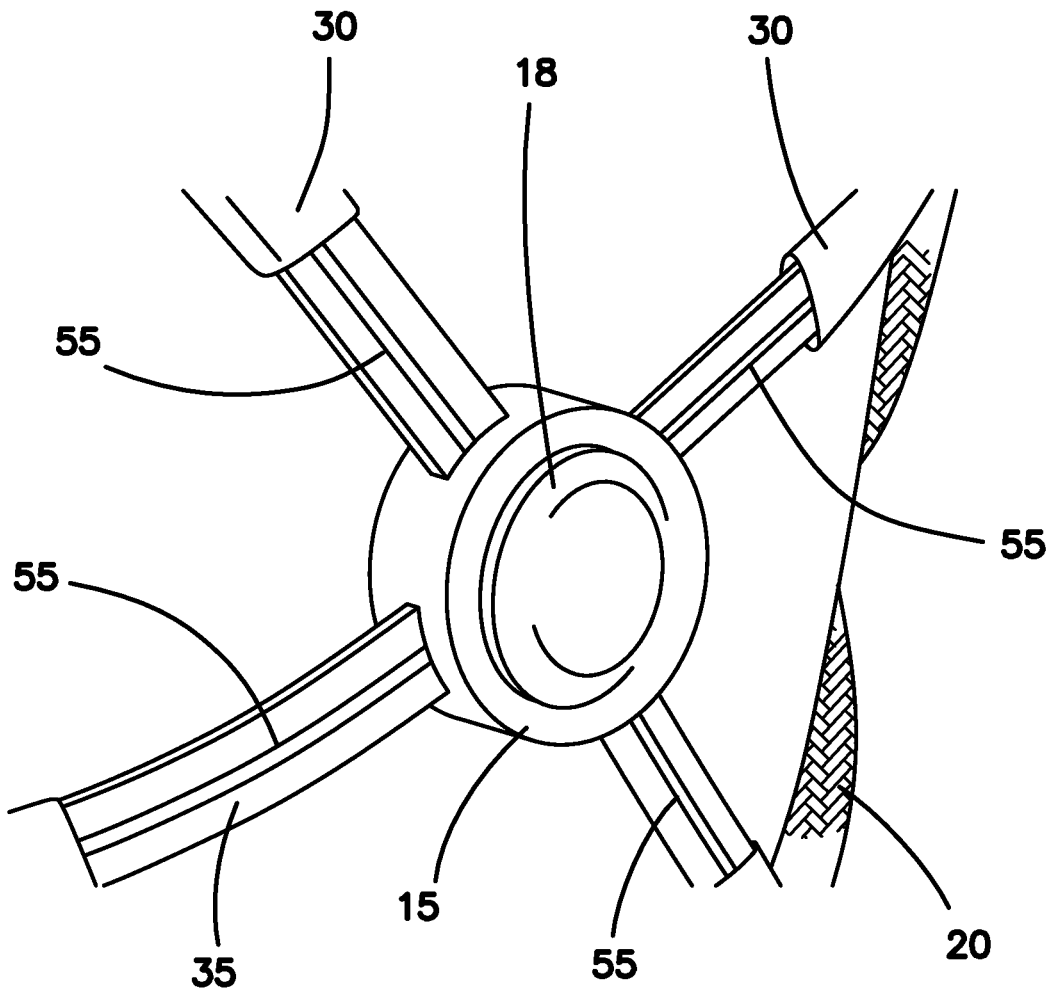
FIG. 5 is a perspective view of a check valve port of the quick deployment cast with polyurethane gel deployed.

In a variant, referring to FIGS. 4 and 5, when the cast is pulled onto a wearer's arm, the check valves 15 automatically open so that air enters the bladder tubes and the polyurethane gel expands and cures so that a rigid or semi-rigid cast is formed. FIGS. 4-5, show the bladders partially cut away for the purpose of illustrating the presence of the polyurethane gel 35 inside the bladders 30. Optionally, the valves 15 may be manually opened.

Figure 6:
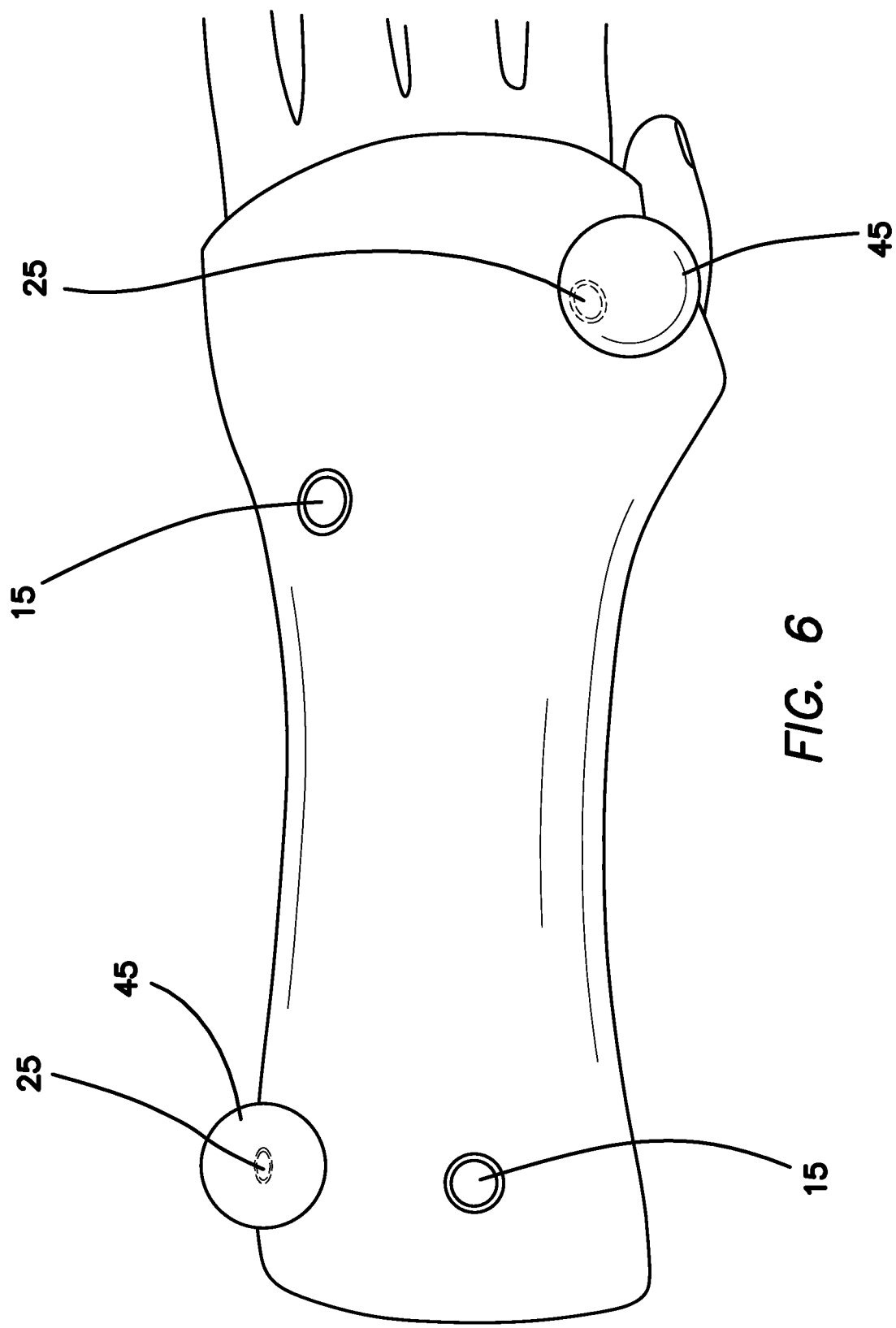
FIG. 6 is a perspective view of the quick deployment cast with balloons deployed.
Figure 7:
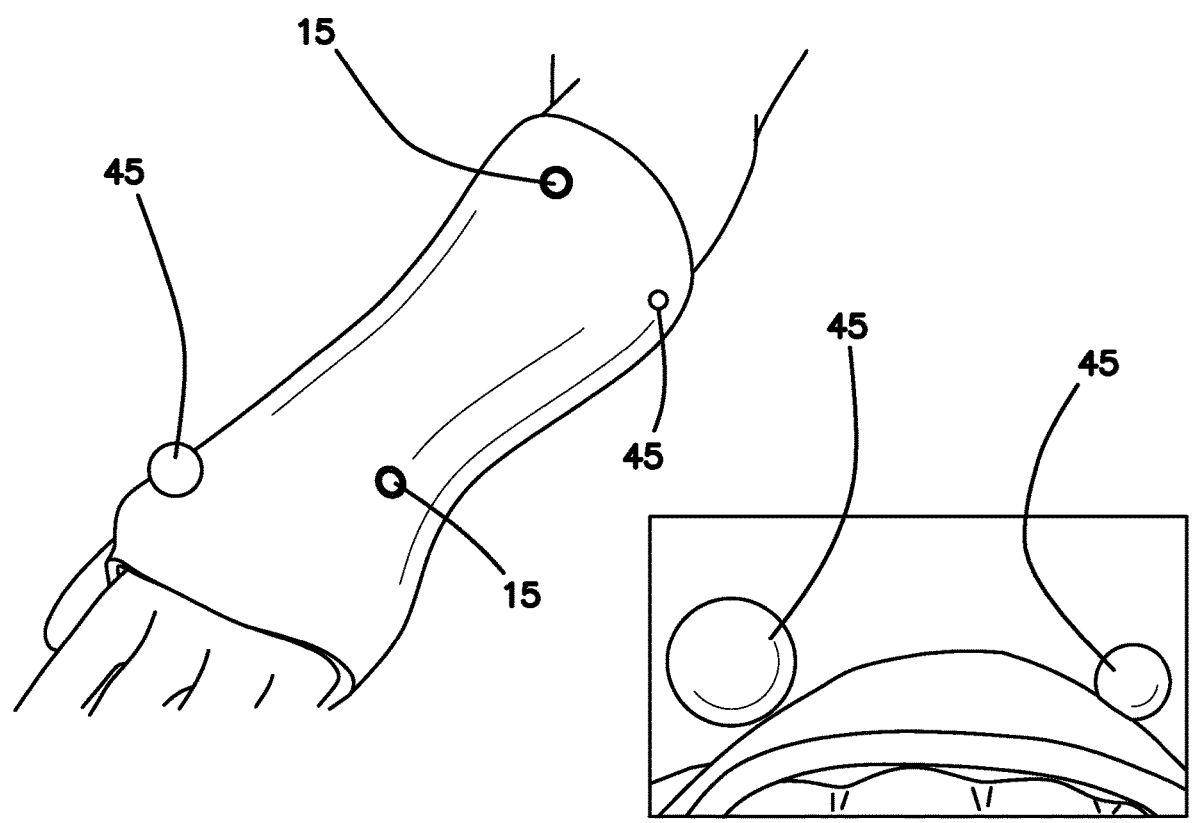
FIG. 7 is a detail view of the quick deployment cast with balloons deployed.
Figure 8:
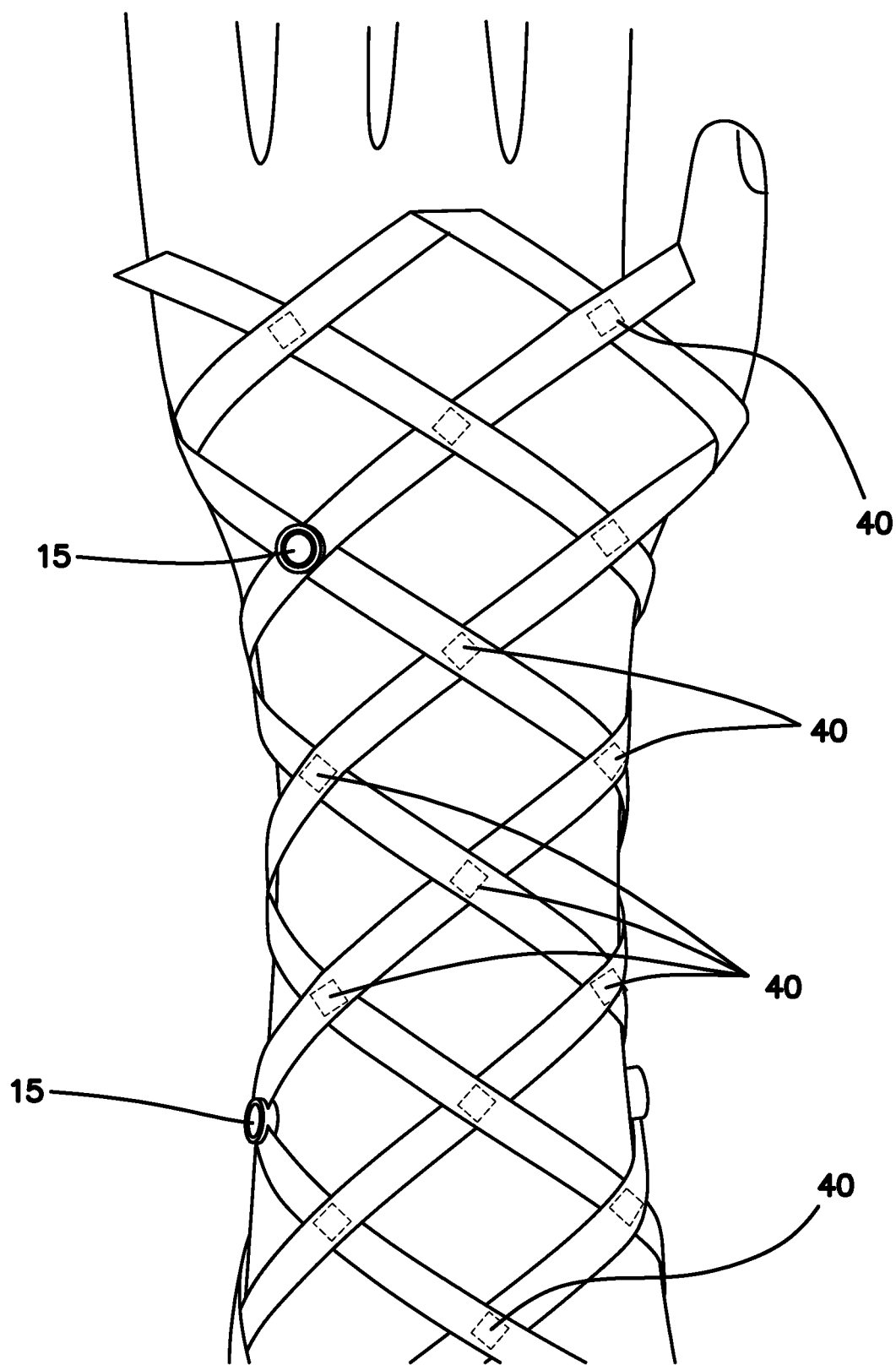
FIG. 8 is a perspective view of the quick deployment cast with illustrating the bactericidal layer attached to the skin-side of the bladder and mimicking the helical and anti-helical pattern of the bladder network.

In another variant, referring to FIG. 8, the bladder tube framework may also contain sensors 40 for detecting tension or pressure, so that when the proper tension on the bladder tubes is reached, the excess or surplus polyurethane may be directed into balloons 45 which are housed in balloon ports 25 as illustrated in FIGS. 6 and 7. After the polyurethane cures, the user may snap the balloons off of the cast manually.

In yet another variant, the sensors 40 also monitor conditions of the cast and the user's limb, such as the integrity, shape and pressure of the cast. Additionally, bio-sensors including, but not limited to pH, pulse, blood-flow, blood oxygen are monitored. The sensors 40 communicate this information to a portable device, such as a smart phone with close-in communication software, which transmits this data to a hospital or other location for monitoring of the patient and cast. Optionally, the cast 10 may function without a sleeve 20. Optionally, the sleeve comprises a flexible compression-sock fabric.

Data derived from monitoring bio-sensor feedback across a volume of users serves as a constantly updating normative baseline for casting metrics and then reconciled with the individual user's baseline to achieve an optimal fit, with proper pressure. An algorithm(s) is derived and serves as a proper casting standard and an early warning to complications of casting. An example would include, but not be limited to, compartment syndrome. The problems that would be addressed are the latitude and variability in traditional casting methods and lack of uniform standards, and the resulting inconsistency and inability to predict complications. In a variant, a processor and memory has computer readable instructions stored thereon configured to cause the processor to receive data from the sensors to determine and monitor proper fit of the cast, progression of healing, and along with the patient's individual baselines normative sensor data, can issue an early warning of complications based on the objective.

In one example embodiment, once deployed, the cast begins collecting data, and when the desired pressure is achieved and the cast is hardened and set, the data set collected, along with normative data, and an algorithm, becomes the baseline for this specific incident. Once deployed, the sensors continue monitoring for deviations from the baseline, so that the cast can alert a monitoring practitioner to problems. In one example, a combination of a decrease in blood oxygen levels at the distal casting point, a weaker pulse, lower blood pressure, decreased pH, and other bio-data that runs automatically through an algorithm, determines via the processor, the earliest possible point, whether there is a threat of compartment syndrome.

Graphene wires 55 or spires are also housed within the bladder tubes and are electrically conductive. The wires 55 may be graphene, graphene composite or graphene oxide or other electrically conductive materials. Electronic pulses or vibrations, for example, at low frequency, may be provided through the wires 55 within the bladder network 30 to promote healing of the broken bone.

Figure 9:
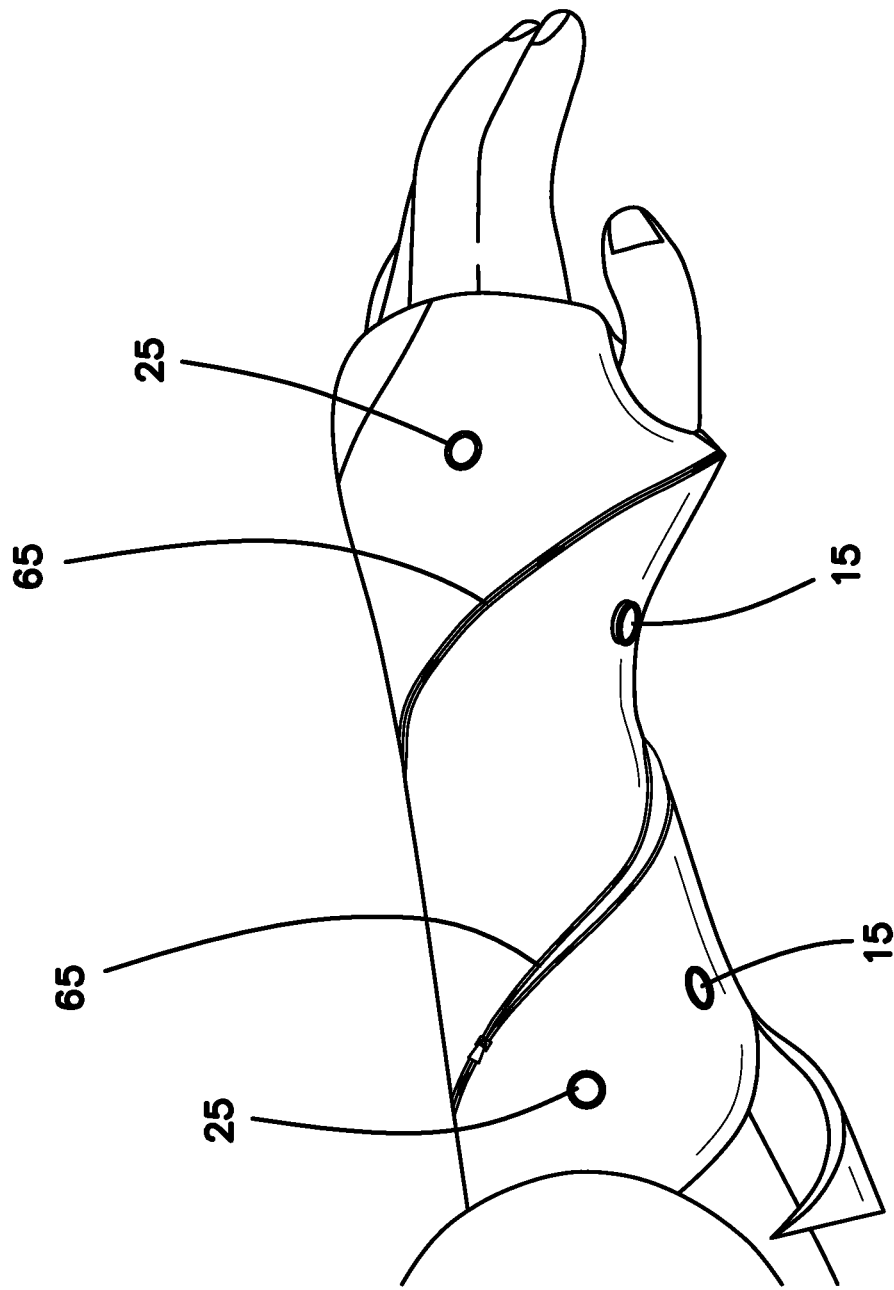
FIG. 9 is a perspective view of the quick deployment cast illustrating seams of the cast, capable of being disassembled via a zipper connection.
Figure 15:
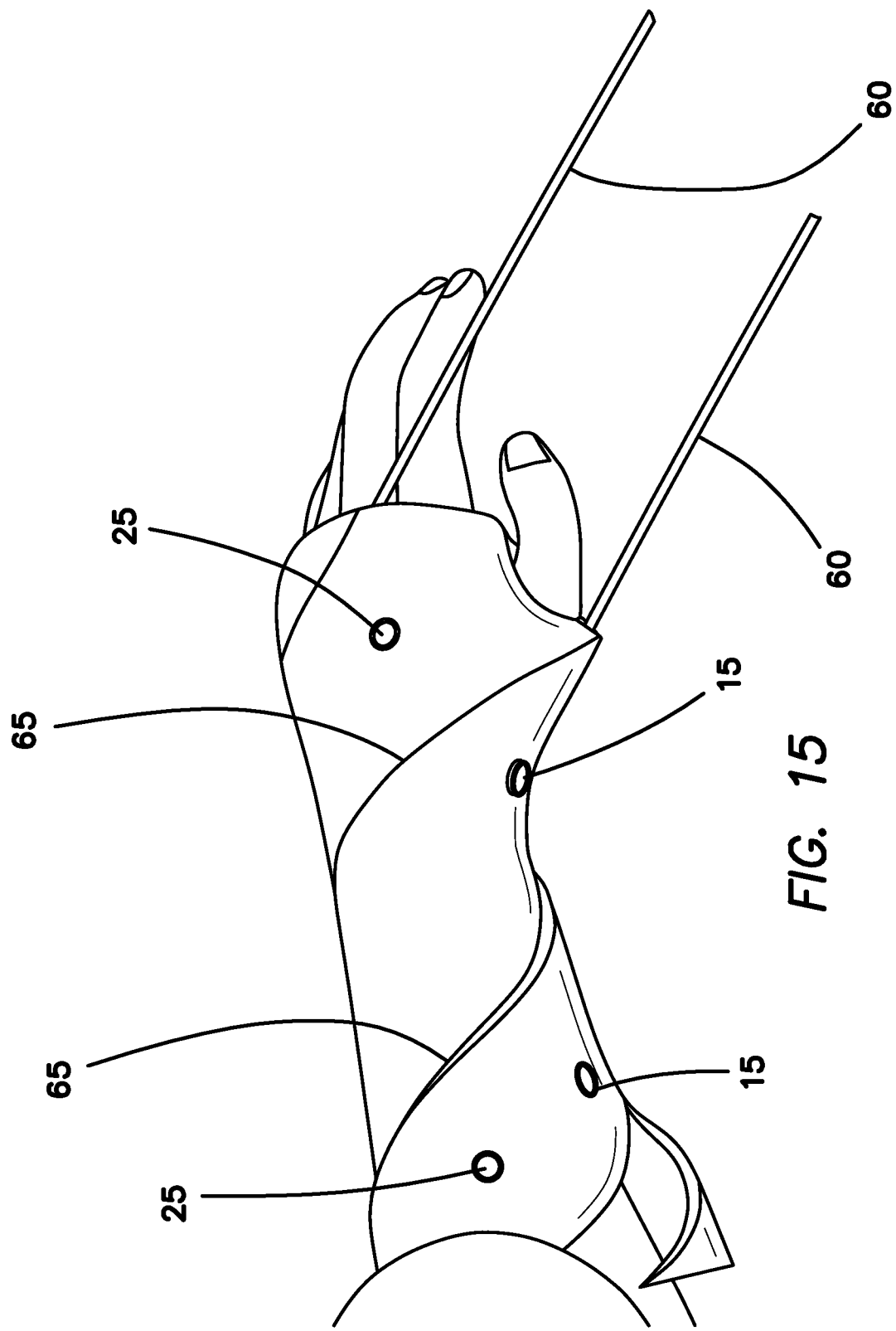
FIG. 15 is a perspective view of wires as part of a zipper-hinge for removal of the quick deployment cast.

In a variant, referring to FIG. 15, to remove the cast, the user pulls two or more wires 60 that cause the outer covering to separate along seams 65. This is analogous to pulling a full-length-pin out of a very long, curved hinge. As a result, the cast comes apart so that the user may easily remove it. In a variant, referring to FIG. 9, a zipper mechanism may be configured to hold together or allow separation of the seams 65, thus providing a mechanism for removing the cast.

Figure 10:
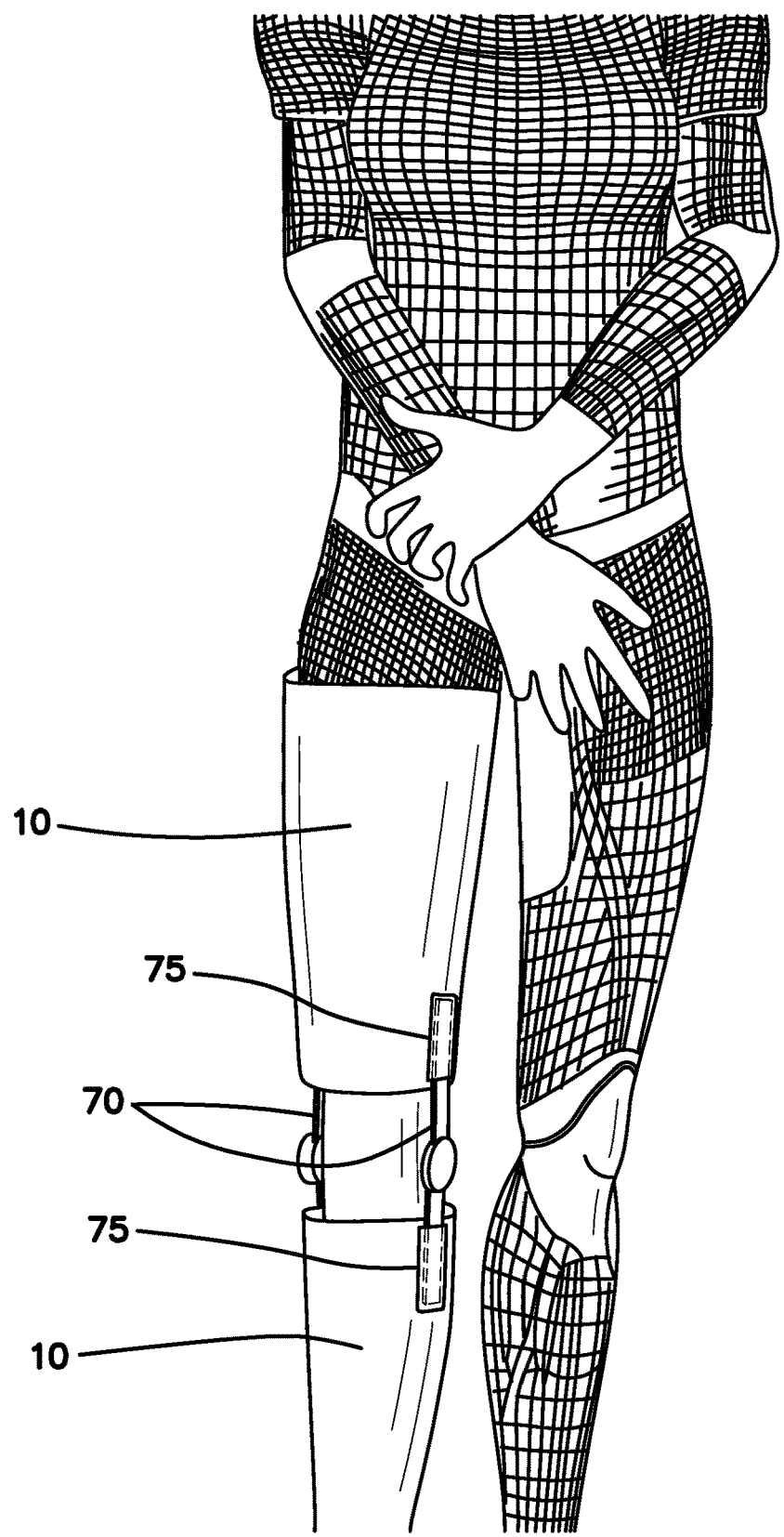
FIG. 10 is a perspective view of an application of the quick deployment cast.
Figure 11:
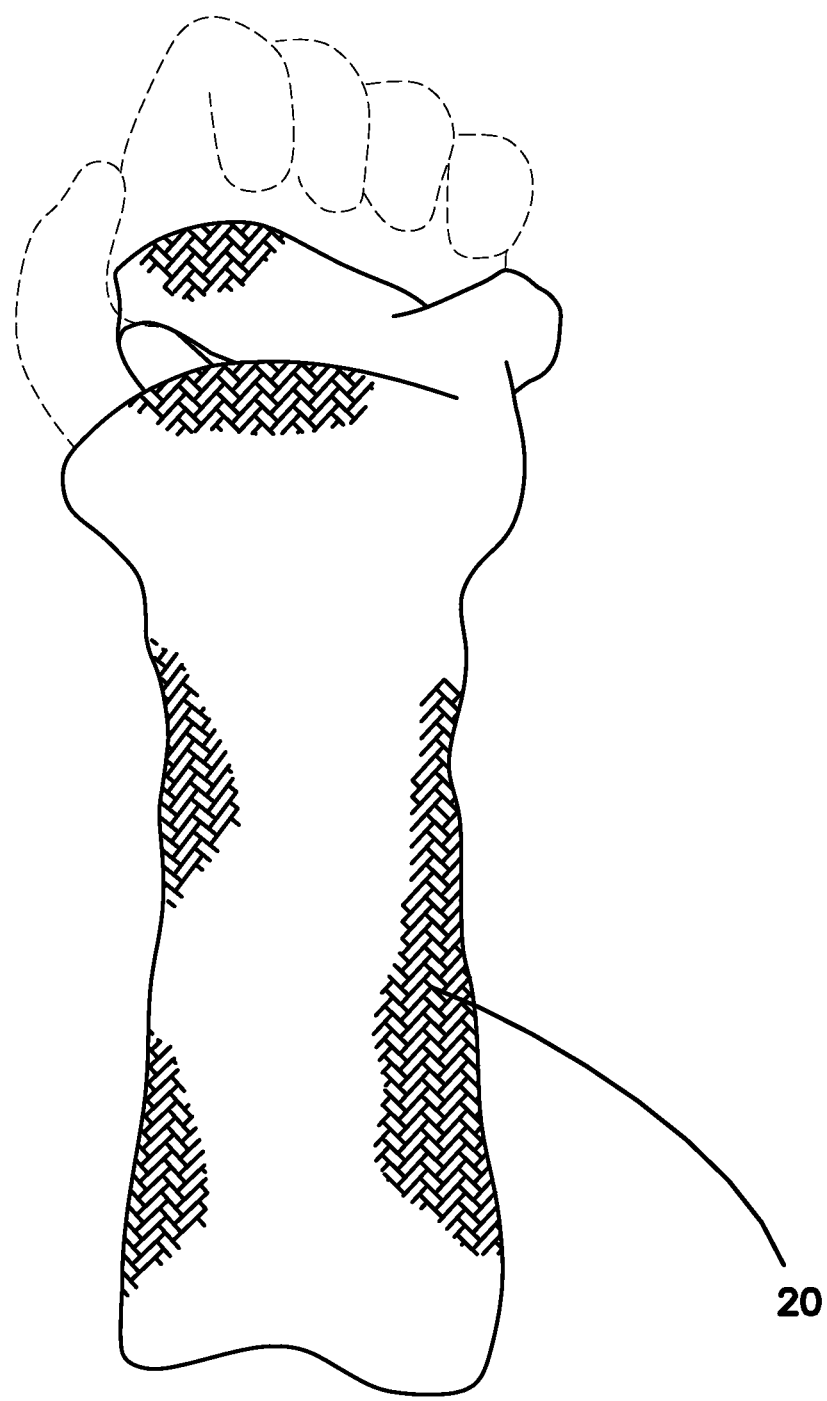
FIG. 11 is top view of a sleeve of the quick deployment cast.
Figure 12:
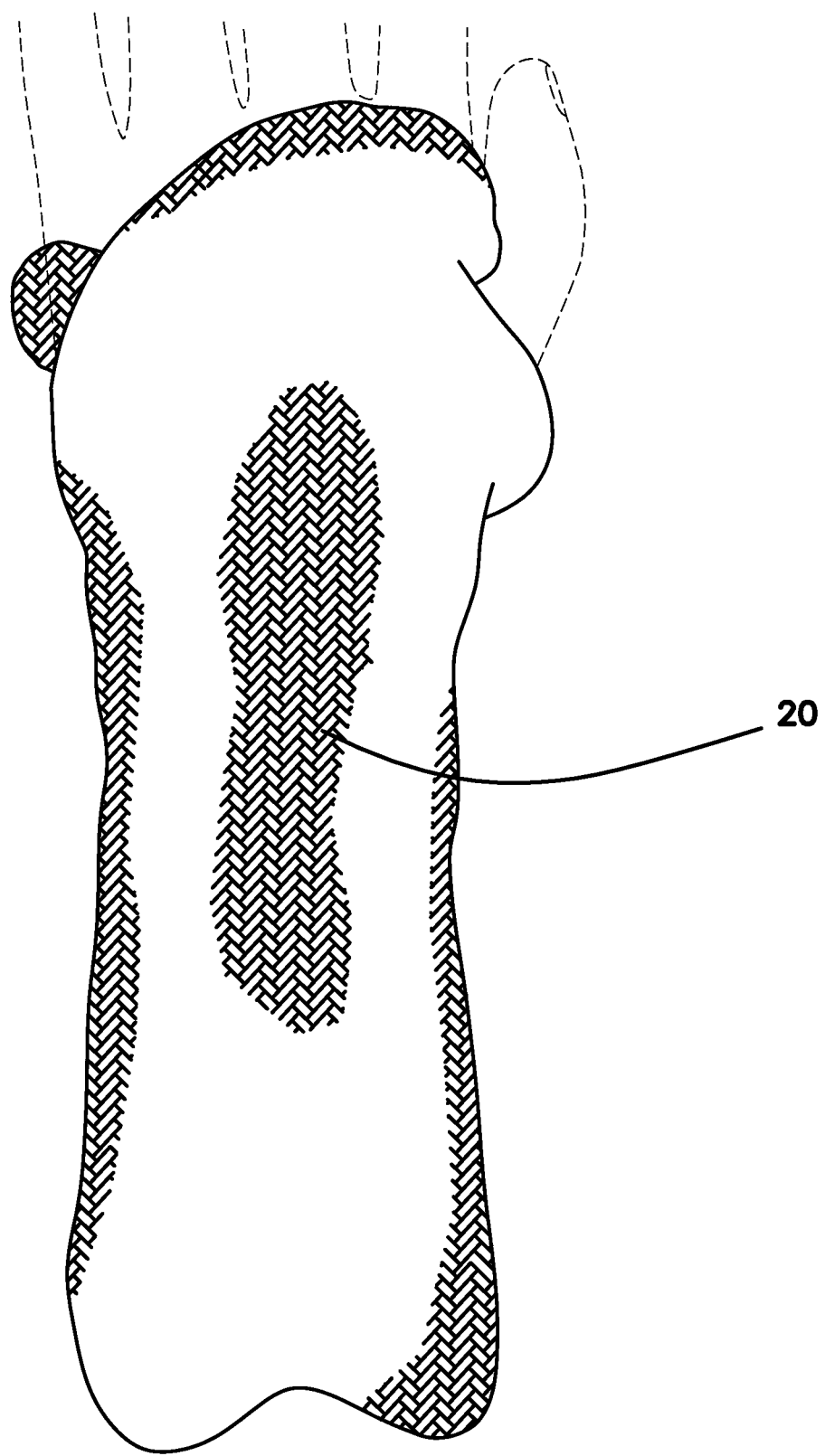
FIG. 12 is a rear view of the a sleeve of the quick deployment cast.

The cast may be constructed in a number of alternative configurations, such as, for example illustrated in FIG. 10, a hinged knee brace 70 inserted in bilateral sleeves 75 between two casts and/or a body cast embodiment.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to achieve the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A quick deployment cast, comprising:
   a bladder network;
   a fluid capable of expanding and hardening when in the presence of a curing agent, stored within the bladder network;
   balloons for receiving excess fluid during deployment of the cast; and
   a mechanism for exposing the fluid to the curing agent.

2. The quick deployment cast of claim 1, further comprising balloon ports on the outside of the sleeve, for housing the balloons.

3. The quick deployment cast of claim 1, wherein the bladder network is disposed within a flexible outer sleeve fitted for a human appendage.

4. A quick deployment cast comprising:
   a bladder network;
   a fluid capable of expanding and hardening when in the presence of air, stored within the bladder network; and
   a mechanism for exposing the fluid to the air.

5. The quick deployment cast of claim 4, wherein the bladder network is disposed within a flexible outer sleeve fitted for a human appendage, and where the quick deployment cast further comprises a second mechanism for removing the quick deployment cast after it has been deployed and its fluid cured, wherein the second mechanism is selected from the group consisting of: a wire embedded within the cast, configured to be pulled out of the cast to cause the cast to separate at seams; a zipper configured to cause the cast to separate at seams when unzipped; and a zipper configured to cause a controlled amount of separation and release of pressure while maintaining integrity, allowing the wearer to benefit from the stability of a cast.

6. A quick deployment cast, comprising:
   a bladder network;
   a fluid capable of expanding and hardening when in the presence of a curing agent, stored within the bladder network;
   a mechanism for exposing the fluid to the curing agent; and
   sensors configured to detect pressure against a limb, and to redirect flow of the fluid to balloons when the cast is fully deployed and proper tension is achieved.

7. The quick deployment cast of claim 6, wherein the bladder network is disposed within a flexible outer sleeve fitted for a human appendage.

8. A quick deployment cast, comprising:
   a bladder network, comprising one or multiple intersecting sets of hollow ducts;
   a fluid capable of expanding and hardening when in the presence of a curing agent, stored within the bladder network; and
   a mechanism for exposing the fluid to the curing agent.

9. The quick deployment cast of claim 8, further comprising a processor and memory with computer readable instructions stored thereon configured to cause the processor to receive data from sensors and determine and monitor proper fit, progression of healing, and early warning of complications based on the sensor data.

10. A quick deployment cast, comprising:
   a bladder network;
   a fluid capable of expanding and hardening when in the presence of a curing agent, stored within the bladder network;
   a mechanism for exposing the fluid to the curing agent;
   electrically conductive spires embedded in the bladder network; and
   sensors for detecting tension or pressure, and the cast configured such that when a predetermined tension on the bladder network is reached, excess fluid is directed into balloons.

11. The quick deployment cast of claim 10, wherein once deployed the cast collects data forming a data set, until a predetermined pressure is achieved and the cast is hardened and set, and the data is stored in a memory as a baseline;
   wherein after the cast is set the sensors continue monitoring for deviations from the baseline and the cast generates an alert upon a detected deviation from the baseline data.

12. The quick deployment cast of claim 10, wherein the bladder network is disposed within a flexible outer sleeve fitted for a human appendage.

\* \* \* \* \*